(12) United States Patent
Tenarvitz

(10) Patent No.: US 6,838,992 B2
(45) Date of Patent: Jan. 4, 2005

(54) METHODS AND SYSTEMS FOR LOCATING SUBJECTS AND PROVIDING EVENT NOTIFICATION WITHIN A TRACKING ENVIRONMENT AND BADGE FOR USE THEREIN

(75) Inventor: Henry J. Tenarvitz, Suttons Bay, MI (US)

(73) Assignee: Versus Technology, Inc., Traverse City, MI (US)

( * ) Notice: Subject to any disclaimer, the term of this patent is extended or adjusted under 35 U.S.C. 154(b) by 0 days.

(21) Appl. No.: 10/394,805

(22) Filed: Mar. 21, 2003

(65) Prior Publication Data

US 2004/0183682 A1 Sep. 23, 2004

(51) Int. Cl.[7] .............................................. G08B 23/00
(52) U.S. Cl. ................................ 340/573.1; 340/573.4; 340/572.1
(58) Field of Search ........................... 340/573.1, 573.4, 340/572.1, 311.2, 825.72, 539.1, 539.16, 286.07, 286.06, 825.29, 825.22

(56) References Cited

U.S. PATENT DOCUMENTS

| | | | |
|---|---|---|---|
| 4,462,022 A | 7/1984 | Stolarczyk | |
| 4,868,859 A | 9/1989 | Sheffer | |
| 4,906,853 A | 3/1990 | Linwood et al. | |
| 4,924,211 A | 5/1990 | Davies | |
| 4,982,176 A | 1/1991 | Schwarz | |
| 5,017,794 A | 5/1991 | Linwood et al. | |
| 5,027,314 A | 6/1991 | Linwood et al. | |
| 5,027,383 A | 6/1991 | Sheffer | |
| 5,119,104 A | 6/1992 | Heller | |
| 5,131,019 A | 7/1992 | Sheffer et al. | |
| 5,218,344 A | 6/1993 | Ricketts | |
| 5,228,449 A | 7/1993 | Christ et al. | |
| 5,276,496 A | 1/1994 | Heller et al. | |
| 5,283,549 A | 2/1994 | Mehaffey et al. | |
| 5,301,353 A | 4/1994 | Borras et al. | |
| 5,355,222 A | 10/1994 | Heller et al. | |
| 5,382,948 A | 1/1995 | Richmond | |
| 5,387,993 A | 2/1995 | Heller et al. | |
| 5,416,468 A | 5/1995 | Baumann | |
| 5,440,559 A | 8/1995 | Gaskill | |
| 5,461,365 A * | 10/1995 | Schlager et al. | ......... 340/573.4 |
| 5,465,082 A | 11/1995 | Chaco | |
| 5,548,637 A | 8/1996 | Heller et al. | |
| 5,570,079 A | 10/1996 | Dockery | |
| 5,572,195 A | 11/1996 | Heller et al. | |
| 5,578,989 A | 11/1996 | Pedtke | |
| 5,610,589 A | 3/1997 | Evans et al. | |
| 5,661,471 A | 8/1997 | Kotlicki | |
| 5,673,032 A | 9/1997 | Ono | |
| 6,087,930 A * | 7/2000 | Kulka et al. | ................ 340/447 |
| 6,104,295 A | 8/2000 | Gaisser et al. | |
| 6,154,139 A | 11/2000 | Heller | |
| 6,353,390 B1 * | 3/2002 | Beri et al. | ............... 340/572.1 |
| 6,462,656 B2 | 10/2002 | Ulrich et al. | |
| 6,512,462 B1 * | 1/2003 | Robineau | ............... 340/825.72 |
| 2002/0059230 A1 | 5/2002 | Hunepohl et al. | |

* cited by examiner

*Primary Examiner*—Anh V. La
(74) *Attorney, Agent, or Firm*—Brooks Kushman, P.C.

(57) ABSTRACT

A method, system and a badge utilized therein utilize both the radio frequency (RF) and infrared (IR) parts of the electromagnetic spectrum to locate subjects (i.e. objects and persons) within a tracking environment. The system includes a battery-operated, microprocessor-based badge for each subject to be located. Each badge automatically transmits: (1) shorter interval, digitized, infrared light signals to identify a delimited area zone of its subject's location; (2) shorter interval, digitized, lower power RF signals to provide a local area zone of its subject's location; and (3) longer interval, digitized, higher power RF signals to provide a wide area zone of its subject's location. Each badge transmits uniquely identifiable IR and higher power RF signals upon actuation of one or more push button switches integrated on the badge or a change of state of one or more external switch connections. Each higher power, longer interval, RF signal is a "supervisory" pulse. This pulse informs a host computer that the badge is in range of an RF receiver and is functional.

28 Claims, 2 Drawing Sheets

METHODS AND SYSTEMS FOR LOCATING SUBJECTS AND PROVIDING EVENT NOTIFICATION WITHIN A TRACKING ENVIRONMENT AND BADGE FOR USE THEREIN

BACKGROUND OF THE INVENTION

1. Field of the Invention

This invention relates to methods and systems for locating subjects and providing event notification within a tracking environment and badges for use therein. In particular, methods and systems are provided for locating subjects within a tracking environment and providing each subject a mechanism to generate notification of varying events to the system in the environment wherein the system includes a badge for each subject to be located. Preferably, each badge is outfitted with one or more push button switches and/or one or more external switch connections.

2. Background Art

An identification system exists whereby a single microprocessor can simultaneously receive sensory input with its subcarrier removed and demodulate the data content on each sensory input. In turn, each sensory input can come from any number of different subcarriers. Such subcarriers include a 40 kHz infrared on/off shift key, and a 447.5 kHz infrared on/off shift key.

The ability to be somewhat media independent has assisted in solving different problems in locating technologies. Such problems include the changing from a low frequency IR carrier to a high frequency IR carrier. The use of higher frequency IR carriers (i.e. 447.5 kHz receivers) are much less likely to obtain optical interference signals caused by the use of newer kinds of fluorescent lighting.

Further use of other subcarriers used with this type of system is a frequency shift keyed (FSK) receiver with appropriate transmitters whose sole combined purpose is to transmit a 10 bit identification code when the transmitter's button is pushed, indicating a special event the user wishes to create. The sensor in this case has a microprocessor that completely demodulates the FSK received code and retransmits that code to a distant microprocessor in such a way that it looks like a demodulated signal from an IR sensor.

U.S. Pat. No. 5,301,353 to Borras et al. discloses a communication system and apparatus wherein the system utilizes one of two different types of communication methods, depending on the location of the user. When the user is in an on-site area, the user communicates via infrared techniques. When the user is in an off-site area, the user communicates using a different communication media, including an RF communication media.

U.S. Pat. No. 5,218,344 to Ricketts discloses a method and system for monitoring personnel in a facility, wherein the system utilizes two different types of communication devices. The system includes a central computer, a plurality of remotely located stationary transceivers, and a portable transceiver unit worn by each monitored individual. In operation, the main computer transmits command signals to a plurality of stationary transceivers using hardwire communication of acoustic, electromagnetic or optical communications. The stationary transceivers then broadcast interrogation signals to the portable transceiver units. The interrogation signals are transmitted via acoustic, electromagnetic or optical transmission methods. The method and system provides a verification of the location of individuals wearing the portable transceiver units.

U.S. Pat. No. 5,228,449 to Christ et al. discloses a system and method for detecting out-of-hospital cardiac emergencies and summoning emergency assistance. The system includes an infrared patient detecting system and an RF communication system. In operation, the infrared system is used to detect the presence and health of the patient. The infrared system provides information to the RF transmitter, which transmits the information to a central computer. The operator of the central computer is then able to monitor the health and presence of the patient via the infrared and radio frequency communication links.

U.S. Pat. Nos. 4,924,211 to Davies and U.S. Pat. No. 5,416,468 to Baumann disclose systems and methods for monitoring personnel, wherein the systems comprise both infrared and radio frequency communication devices.

U.S. Pat. Nos. 4,462,022; 4,982,176; 5,570,079; 5,283,549; and 5,578,989 show security systems using local infrared detecting devices which communicate with a central monitoring station via a radio frequency communication link.

U.S. Pat. No. 5,027,314 discloses a system and method for tracking a number of subjects in a plurality of areas. The system includes a plurality of transmitters associated with the subjects, a plurality of receivers associated with the areas and a centralized processor for determining in which of the areas the transmitter and, consequently, the subjects are located. Each transmitter transmits a light-based signal, such as an infrared signal, representative of an identifying code unique to the transmitter. Each receiver validates the signal to determine whether the signals are representative of the unique identifying codes associated with the transmitters. The centralized processor records the validated signals and receivers, scans the receivers and accumulates areas and badge counts for each area.

U.S. Pat. No. 5,548,637 discloses an automated method and system for providing the location of a person or object (i.e. a subject) in the form of a message in response to a telephone caller's inquiry. The method and system may connect the caller directly to the telephone extension located nearest the subject of interest. A transmitter, such as an infrared transmitter, is attached to each subject to be monitored within a defined area such as a building. A number of receivers or sensors track the location of the subject within the building. The locations are stored in a database. In one form of the invention, as each transmitter is transported throughout the building, the system continually updates the transmitter location in the database.

U.S. Pat. No. 5,572,195 discloses a method and system for tracking an locating objects wherein the system includes a computer network, such as a local area network, a computer connected to the computer network, infrared sensors, and interface circuitry connecting the computer network to the infrared sensors. The infrared sensors are adapted to receive unique identifying codes from infrared transmitters and then provide the codes to the interface circuitry. In turn, the codes are then provided to the computer network. The invention may be implemented using an object identifier variable-based protocol such as SNMP (Simple Network Management Protocol). The system may include an external device controller, such as a relay controller, for controlling a physical device such as an electronic door lock within the environment.

U.S. Pat. No. 5,387,993 discloses various methods of transmitting data and control information such as battery life for badges (TAGs) to optical (i.e. infrared) receivers of an optical locator system. In one of the methods, the badges are "motion-detectable" and have a sleep mode. The badges are reprogrammable with identifying information about the objects to which they are attached. Each badge activates the sleep mode, thereby reducing its normal power consumption. Each TAG will reactivate the sleep mode when motion is detected by the motion detector, thereby returning the battery power level to normal.

U.S. Pat. No. 5,119,104 discloses a radiolocation system for multipath environments, such as for tracking objects in a facility, includes an array of receivers distributed within the tracking area, coupled to a system processor over a LAN. A TAG transmitter located with each object transmits, at selected intervals, spread spectrum TAG transmissions including at least a unique TAG ID. Object location is accomplished by time-of-arrival (TOA) differentiation, with each receiver including a TOA trigger circuit for triggering on arrival of a TAG transmission, and a time base latching circuit for latching the TOA count from an 800 MHz time base counter. In a low resolution embodiment, each receiver of the array is assigned a specific location-area, and receives TAG transmissions almost exclusively from TAGs located in that area, thereby eliminating the need for any time-of-arrival circuitry.

U.S. Pat. No. 5,276,496 discloses an optical receiver for use with an optical location system that locates a target in a defined area. A spherical lens is placed over the area. The area is divided into sections, with a sensor associated with each section. These sensors receive light transmitted through the lens, and are positioned relative to each other and with respect to the lens, such that each sensor receives emitted light from the same size section if the target is located in its section. The height of each sensor may be adjusted so that each sensor receives light of the same intensity if the target is located in its section.

U.S. Pat. No. 5,355,222 discloses an optical location system for locating the position of a moving object in a defined area. An optical transmitter is attached to the moving object. A stationary receiver has a number of sensors for receiving a signal from the transmitter. One sensor has a field of view of the entire area. Other sensors have partially blocked fields of view, with the blocking being accomplished with nonopaque strips of decreasing width. These strips are arranged so that the detection or nondetection of light by the sensors can be digitally coded in a manner that corresponds to sections of the area.

U.S. Pat. No. 4,906,853 discloses a control apparatus for triggering a periodic pulse at random times comprising a timer for variably issuing the periodic pulse in a defined time cycle and a signal generator for variably generating an output voltage within the defined cycle. The signal generator has a light sensitive component for varying in time the generation of the output voltage in proportion to the intensity of visible light incident on the light sensitive component. The apparatus also includes a circuit for applying the generated output voltage to the timer for triggering the issuance of the periodic pulses.

U.S. Pat. No. 5,017,794 discloses apparatus including a time for generating a periodic pulse in a defined time cycle in response to a control signal, and a signal generator for variably generating the control signal within the defined cycle. The signal generator includes a light sensitive component for varying in time the generation of the control signal in proportion to the light incident on the light sensitive component for a portion of the defined cycle.

U.S. Pat. No. 6,154,139 discloses a method and system for locating subjects within a tracking environment utilizing an IR or line-of-sight signal and a wide area, high power RF signal.

U.S. Pat. No. 6,104,295 discloses an electronic band tag and method of storing ID information therein.

U.S. Pat. No. 5,131,019 discloses a system for interfacing an alarm reporting device with a cellular radio transceiver.

U.S. Pat. Nos. 5,027,383 and 4,868,859 both disclose a supervised, interactive alarm reporting system.

U.S. Pat. No. 5,661,471 discloses an emergency alert system for a protected region employing RF and non-RF signaling.

Published U.S. patent application Ser. No. 2002/0059230 discloses an add-on apparatus which allows pre-installed access control systems to act as asset management systems. This apparatus can make use of existing access control panels, networks, and sometimes access control system readers and other infrastructure. The readers receive periodic signals from active tags associated with particular assets. When an asset moves to a new location, the associated active tag emits a signal (one of the continual stream of periodic signals that it emits). That signal is detected by a nearby reader for the first time. The reader transmits information derived from the signal to the apparatus, which then changes state to indicate that the asset is now in its domain.

The following U.S. patents are also related to the present invention: U.S. Pat. Nos. 5,673,032; 5,610,589; 5,465,082; 5,440,559; 5,382,948; and 6,462,656.

There are a number of drawbacks in using IR signals including: (1) if a badge is covered, its IR signal is blocked; and (2) an IR receiver must be placed in every room, thereby increasing installation cost.

SUMMARY OF THE INVENTION

An object of the present invention is to provide improved methods and systems for locating subjects and providing event notification within a tracking environment and badge for use therein.

In carrying out the above object and other objects of the present invention, a method for locating subjects within a tracking environment is provided. The method includes the steps of, for each subject, providing a badge capable of transmitting a shorter interval, lower power, local area signal including a unique badge ID and a longer interval, higher power, wide area signal also including the unique badge ID. An array of receivers is provided distributed within the tracking environment. The array of receivers includes at least one receiver for receiving the shorter interval, lower power, local area signal and the longer interval, higher power, wide area signal. The method further includes generating a wide area detection packet including the unique badge ID in response to each received wide area signal, generating a local area detection packet including the unique badge ID in response to each received local area signal, and determining the location of each badge and its associated subject based on the identity of the at least one receiver for the badge as represented by its local area or wide area detection packets.

The signals may be electromagnetic signals, such as radio frequency (RF) signals and the at least one receiver may be at least one RF receiver.

Further in carrying out the above object and other objects of the present invention, a system is provided for locating subjects within a tracking environment. The system includes, for each subject, a badge capable of transmitting a shorter interval, lower power, local area signal including a unique badge ID and a longer interval, higher power, wide area signal also including the unique badge ID. A receiver assembly includes an array of receivers distributed within the tracking environment. The array of receivers includes at least one receiver for receiving a plurality of the local area and wide area signals. The receiver assembly generates a wide area detection packet including the unique badge ID in response to each received wide area signal and a local area detection packet including the unique badge ID in response to each received local area signal. A data communications controller is coupled to the receiver assembly for collecting the wide area and local area detection packets. A location processor is coupled to the controller for receiving the collected detection packets and for determining the location of each badge and its associated subject based on the identity of the at least one receiver for the badge as represented by its wide area and local area detection packets.

The signals may be electromagnetic signals, such as radio frequency (RF) signals and the at least one receiver may be at least one RF receiver.

Each badge may includes an RF transmitter for transmitting its RF signals and a single controller for controllably modulating both the local area and wide area signals with its unique badge ID.

The single controller may be a microprocessor-based controller.

The receiver assembly may include a collector coupled to the at least one RF receiver for controllably demodulating the received RF signals to obtain the wide area and local area detection packets.

The collector may include a single microprocessor for controllably demodulating the received RF signals.

Yet still further in carrying out the above object and other objects of the present invention, a method for locating subjects within a tracking environment is provided. The method includes the steps of, for each subject, providing a badge capable of transmitting a substantially line-of-sight signal including a unique badge ID and substantially non-line-of-sight signals also including the unique badge ID. An array of receivers is provided distributed within the tracking environment. The array of receivers includes a first set of receivers for receiving both shorter interval, lower power, local area, substantially non-line-of-sight signals and longer interval, higher power, wide area, substantially non-line-of-sight signals and a second set of receivers. Each of the second set of receivers receive substantially line-of-sight signals. The method further includes generating a wide area detection packet including the unique badge ID in response to each received higher power, substantially non-line-of-sight signal, generating a local area detection packet including the unique badge ID in response to each received lower power, substantially non-line-of-sight signal, and generating a delimited area detection packet including the unique badge ID in response to each received substantially line-of-sight signal. The location of each badge and its associated subject is determined based on the identity of the first and second sets of receivers for the badge as represented by its delimited area, local area or wide area detection packets.

The substantially line-of-sight and non-line-of-sight signals may be electromagnetic signals.

The substantially non-line-of-sight signals may be radio frequency (RF) signals and each of the first set of receivers may be an RF receiver.

The substantially line-of-sight signals may be infrared (IR) signals and each of the second set of receivers may be an IR receiver.

Further in carrying out the above object and other objects of the present invention, a system for locating subjects within a tracking environment is provided. The system includes, for each subject, a badge capable of transmitting substantially line-of-sight signals including a unique badge ID and substantially non-line-of-sight signals also including the unique badge ID. A receiver assembly includes an array of receivers distributed within the tracking environment. The array of receivers includes a first set of receivers for receiving a plurality of substantially non-line-of-sight signals. The receiver assembly generates a wide area detection packet including the unique badge ID in response to each received higher power, substantially non-line-of-sight signal and a local area detection packet including the unique badge ID in response to each received lower power, substantially line-of-sight signal. The array of receivers also includes a second set of receivers. Each of the second set of receivers receives substantially line-of-sight signals. The receiver assembly generates a delimited area detection packet including the unique badge ID in response to each received substantially line-of-sight signal. A data communications controller is coupled to the receiver assembly for collecting the wide area, local area and delimited area detection packets. A location processor is coupled to the controller for receiving the collected detection packets and for determining the location of each badge and its associated subject based on the identity of the first and second sets of receivers for the badge as represented by its wide area, local area or delimited area detection packets.

The substantially line-of-sight and non-line-of-sight signals may be electromagnetic signals.

The substantially non-line-of-sight signals may be radio frequency (RF) signals and each of the first set of receivers is an RF receiver.

The substantially line-of-sight signals may be infrared (IR) signals and each of the second set of receivers may be an IR receiver.

Each badge may include an RF transmitter for transmitting its RF signals, an IR transmitter for transmitting its IR signal and a single controller for controllably modulating the RF and IR signals with its unique badge ID.

The single controller may be a microprocessor-based controller.

The receiver assembly may include a collector coupled to the RF and IR receivers for controllably demodulating the received RF and IR signals to obtain the wide area, local area and delimited area detection packets.

The collector may include a single microprocessor for controllably demodulating the received RF and IR signals.

Still further in carrying out the above object and other objects of the present invention, a badge capable of transmitting substantially line-of-sight signals including a unique badge ID and substantially non-line-of-sight signals also including the unique badge ID is provided. The badge includes a first transmitter for transmitting a plurality of substantially non-line-of-sight signals including a longer interval, higher power, wide area, substantially non-line-of-sight signal and a shorter interval, lower power, local area, substantially non-line-of-sight signal. The badge further includes a second transmitter for transmitting a plurality of substantially line-of-sight signals.

The substantially line-of-sight and non-line-of-sight signals may be electromagnetic signals.

The substantially non-line-of-sight signals may be radio frequency (RF) signals.

The substantially line-of-sight signals may be infrared (IR) signals.

The first transmitter may include an RF transmitter for transmitting the RF signals. The second transmitter may include an IR transmitter for transmitting the IR signal. The badge may further include a single controller for controllably modulating the RF and IR signals with its unique badge ID.

The single controller may be a microprocessor-based controller.

The above object and other objects, features, and advantages of the present invention are readily apparent from the following detailed description of the best mode for carrying out the invention when taken in connection with the accompanying drawings.

DETAILED DESCRIPTION OF THE PREFERRED EMBODIMENTS

Figure 1:
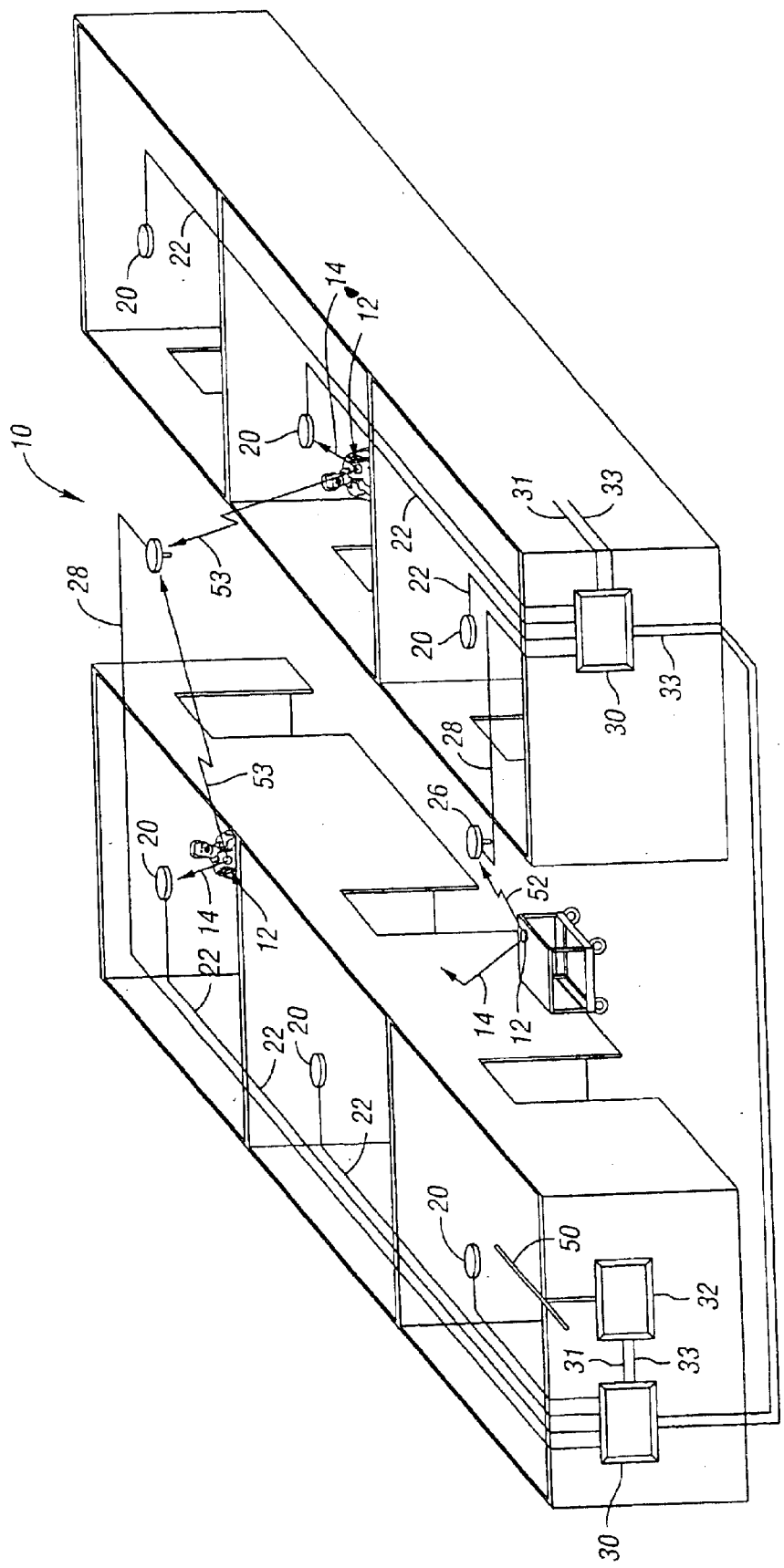
FIG. 1 is a schematic overview diagram illustrating the method and system of the present invention.
Figure 2:
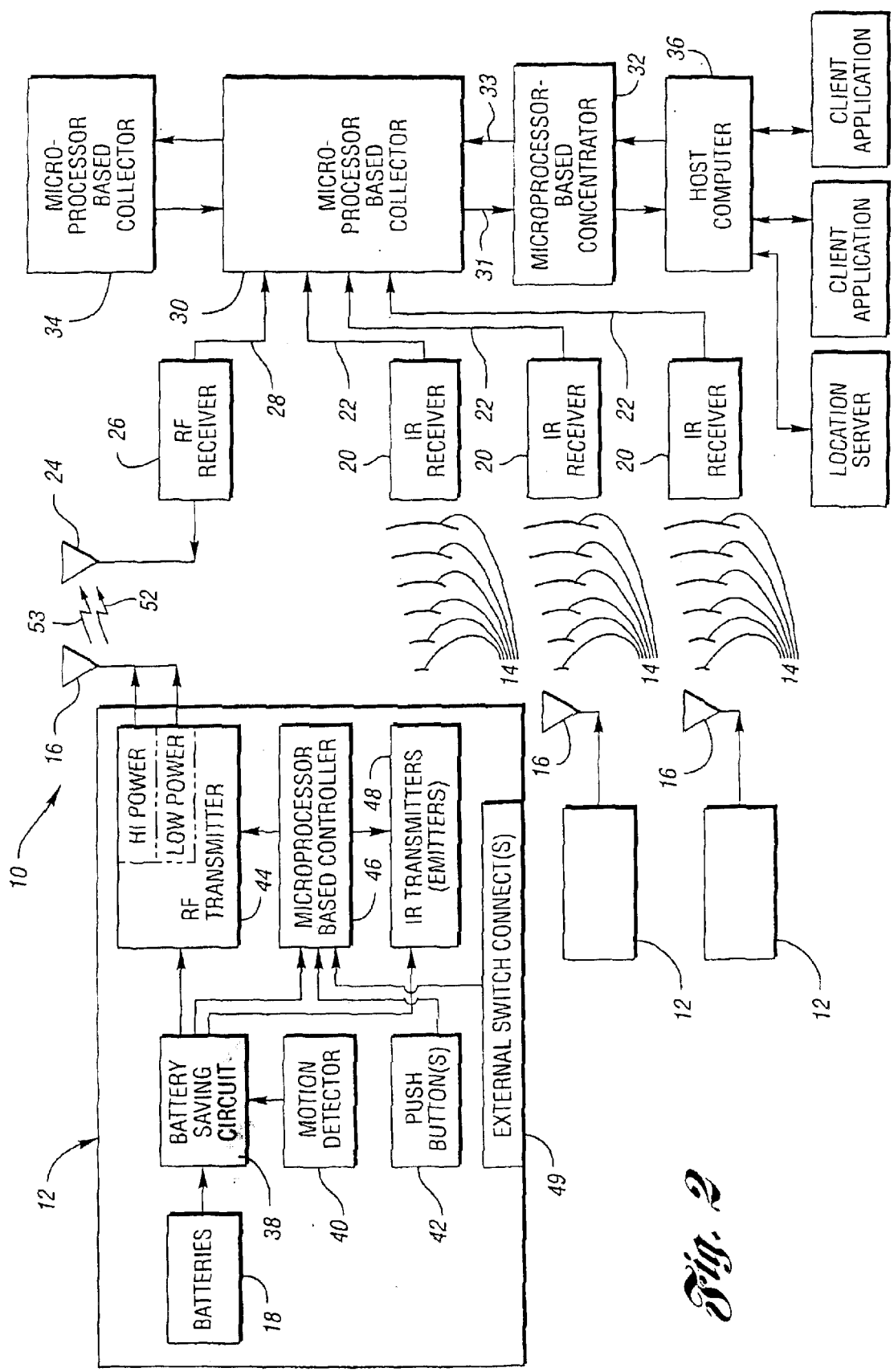
FIG. 2 is a schematic block diagram also illustrating the method and system of the present invention.

Referring now to FIGS. 1 and 2, there is illustrated a system, generally indicated at 10, for locating subjects (i.e. persons and objects) in a tracking environment. In general, the system is a combined infrared and radio frequency locating system which is adapted for use not only in medical applications, but also in non-medical applications. The system 10 is a fully automatic data collection system which provides real-time location information of personnel or equipment (i.e. subjects). Typically, information is collected using an in-ceiling and/or in-wall receiver network connected with common telephone-type wire to make accurate decisions and execute the appropriate responses. Typically, the components of the system 10 are relatively simple and modular.

In general, the system 10 includes a plurality of badges, each of which is generally indicated at 12. Each badge 12 is provided for each subject to be tracked within the tracking environment. In general, each badge emits one or more hemispheres of digitally encoded infrared (i.e. IR) light as indicated by lines 14. Preferably, the digitally encoded infrared light includes a 42 bit packet having a fixed 16 bit ID plus other network information. Typically, the effective range of such infrared light is approximately 15 to 18 feet. The infrared light is a substantially line-of-sight signal.

Each badge 12 also transmits radio frequency (i.e. RF) signals 52 and 53 via an antenna 16. The RF signals 52 and 53 generated by an RF transmitter 44 are of two different field strengths. A lower power or local area RF transmission 52 is tuned to be below the signal strength threshold regulated by the FCC for data transmission. This scheme allows the badge 12 to transmit at a short interval, typically interlaced between each automatically generated IR transmission 14.

The lower power RF signal is almost as accurate as IR, but is a much more robust signal. The lower power RF signal is particularly useful to: 1) monitor a person who is leaving the tracked area with their badge; 2) provide an inexpensive "idea" of where the subject is located; and 3) monitor a person who is leaving the tracked area with a hidden piece of equipment.

A higher power or wide area RF signal 53 is also generated at a longer time interval, typically greater than 10 seconds, as a "supervisory" pulse. This pulse informs the host computer that the badge is both present and fully functional. The high power RF signal 53 is also sent when any one of multiple push button switches 42 (internal to the badge 12) is pressed or external switch connects or inputs 49 state changes have been identified.

The alternating digitized infrared light 14 and the radio frequency signals 52 and 53 contain badge identification data, switch state changes, and condition of a battery 18 contained within each of the badges 12.

The system 10 also includes a receiver assembly including a plurality of infrared receivers 20 which are utilized to receive the badges' infrared signals and transmit coded transmission data along twisted pair connections 22.

The radio frequency signals 52 and 53 emitted by the antennas 16 are received by an antenna 24 of a radio frequency receiver 26 which comprises a receiver having a range of approximately 100 to 200 feet in all directions. The radio frequency receiver 26 converts encoded signals emitted by the badges or transmitters 12 into electrical signals which are transmitted via a single twisted pair connection 28.

The signals appearing along the connection 28, as well as the connections 22, are received by a microprocessor-based collector 30 of the receiver assembly which takes the incoming data packets, buffers them and prepares them for transfer to a concentrator 32 of the system 10. The collector 30 assembles data received from the receivers 20 and 26 into a larger network-ready packet. This network-ready packet is then relayed along a twisted wire pair 31 to the concentrator 32. Typically, software for the collector 30 is uploaded via the concentrator 32 along a connection 33. Typically, the microprocessor-based collector 30 can be connected to up to 24 receivers such as the receivers 20 and the receiver 26.

The concentrator 32 typically scans the collector 30 as well as any other collectors such as a collector 34 connected in a single daisy chain or multi-drop configuration to the concentrator 32. In turn, the collector 34 is connected to other receivers (not shown) of the infrared and RF types.

The system 10 also includes an appropriately programmed host computer 36 which receives and processes data packets collected by the concentrator 32.

Referring in detail now to the left side of FIG. 2, each of the badges 12 typically includes the battery 18 which may comprise a lithium 3 volt-type battery. The badge 12 also includes a battery-saving circuit 38 connected to the battery 18 and to a motion detector 40 wherein IR transmissions from the badge 12 are triggered at a higher frequency when the badge 12 is in motion and are reduced in frequency when the badge 12 is at rest to preserve battery life.

Each badge 12 may include one or more push buttons 42 which are manually operable and can be used to request pages or to send alerts by means of the high power, wide area signal 53 generated by a radio frequency transmitter 44 under the control of a microprocessor-based controller 46.

Each badge 12 may also include one or more external switch connects 49 which may be used to trigger processes preprogrammed on the host computer 36 by means of the high power, wide area signal 53 generated by the radio frequency transmitter 44 under control of the microprocessor-based controller 46.

While the infrared transmissions from the badge 12 are location specific since infrared signal transmissions do not penetrate walls or floors, the radio frequency signals 52 transmitted or emitted by the radio frequency transmitter 44 under the control of the controller 46 do penetrate walls and floors. The radio frequency transmitter 44 also produces high power, wide area supervisory signals 53 at a predetermined application specific interval typically greater than 10 seconds and page request/alert signals substantially instantaneously upon depression of a push button switch 42 or a change at the external switch connect 49.

The microprocessor-based controller 46 controls the RF transmitter 44 to modulate data including preset, unique identification codes (i.e. badge ID) at the appropriate power setting. For example, a radio frequency data modulation routine provided by the controller 46 typically holds an oscillator contained within the RF transmitter 44 on the entire period the push button switch 42 or external switch connect 49 is activated. Preferably, the RF transmitter 44 under the control of the controller 46 uses frequency shift keyed modulation.

In like fashion, an IR transmitter or emitter 48 of the badge 12 also under control of the controller 46 modulates the IR transmissions from the transmitter 48. For example, a 447.5 kHz signal, when emitting a carrier on pulse, will turn the LED of the transmitter 48 on and off for so many microseconds (typically 120 microseconds).

The RF receiver 26 typically uses modulating current loop transmission signaling technology for high reliability. Typically, the receiver 26 can be located up to 1,000 feet from its associated collector 30 using standard unshielded twisted pair telephone-type wire. While the receiver 26 and the receivers 20 are typically mounted in acoustic tile, they may be also mounted on walls or other convenient locations.

The modulation process provided for each badge 12 by its controller 46 is reversed within each microprocessor-based collector 30. Each collector 30 removes the subcarrier from the signals appearing on connections 28 and 22, thereby leaving the data as demodulated serial data. The microprocessor within the collector 30 then demodulates the ID data received. It then passes this data upstream such that the only relevant information that the signal came from a radio frequency receiver such as the radio frequency receiver 26 or an infrared receiver such as one of the infrared receivers 20 is determined by the software contained within the host computer 36 when the particular receivers 26 and 20 are programmed into the system 10. Not only is the system 10 knowledgeable as to the type of receiver the data is received from, but also its location.

Typically, the host computer 36, when appropriately programmed, can process the last known infrared location for purposes of servicing the subject associated with badge 12 that has detected a push button switch 42 or external switch 49 activation.

For example, since bathrooms are places where it can be difficult to place infrared receivers 20 and where people may object to such a receiver being present, a push of the push button 42 by a person within such a bathroom will require the host computer 36 to find the last known infrared receiver reception (which is likely to be outside the restroom). Hence, the proper service can be delivered to the person who pressed the push button 42.

As described above, the system includes a badge for each subject to be located and wherein each badge emits or transmits substantially line-of-sight and substantially non-line-of-sight signals. The signals in the preferred embodiment are RF and IR. The benefits of IR are two-fold. Firstly, the cost of reception and transmission components are low. Secondly, the benefit of IR is its high line-of-sight nature. The use of this feature enables processing software to infer that the signal is highly proximate (line-of-sight or almost line-of-sight) to the transmitter. The ability to make this inference creates a much more precise location fix.

The use of RF obviates the requirement that a badge is line-of-sight when an internal push button switch on the badge is actuated or an external switch change input is detected. Further, the requirement to have a receiver in every room is obviated and an RF receiver that receives "switch state change events" per every 10, 20 or 30 rooms is reasonable observing current FCC regulation and available low cost RF components.

As described above, the system includes a badge for each subject to be located and wherein each badge may include push button switches or external switch connections that causes RF and IR signals to be emitted upon a "switch state change" event providing each subject with a mechanism to generate notification of varying types to the system.

In the event the IR signal is attenuated, the processing software can process preprogrammed instructions to be executed in the event of that particular "switch state change" event having received the RF component of the signal and having stored the last known IR location of the badge.

As described above, the system includes a badge for each subject to be located and wherein the badge includes a single microprocessor which substantially develops the signals for both emitters or transmitters (RF oscillator and IR LEDs). The data encoding routines are substantially identical. However, the subroutines for the sub-carriers may differ. For example, a 447.5 kHz signal when emitting a carrier ON pulse, will turn the IR LED on and off for so many microseconds (typically 120 $\mu$s) whereas the RF data modulation routine might hold the carrier (i.e. oscillator) ON for the entire period. This process will conserve battery life in the badge by reducing the "duty cycle" of the IR LEDs.

The process is reversed at the microprocessor/receiving side. That is, a single microprocessor is used with multiple receivers that remove the subcarrier from the signal leaving the data as demodulated serial data. The receiver microprocessor then demodulates the ID received. It then passes on the data upstream such that the only relevant information that the signal came from RF or IR is determined by the software when the receiver is programmed into the system. This is referred to at setup or installation. It is only at this time that the system is knowledgeable as to the type of receiver it is (as well as its location).

In this way, a single microprocessor is modulating different signals either simultaneously or staggered. Different receivers sensitive to different media and sub-carriers and a single microprocessor demodulate data virtually independent of the media. Data then flows through the system without any knowledge of the data routing components along the way with the final software making expert inferences then knowledgeable as to the media the identification signal came in from.

As described above, an embodiment of the method includes the steps of providing, for each subject, a badge for transmitting both a substantially line-of-sight signal including a unique badge ID and a substantially non-line-of-sight signal also including the unique badge ID. An array of receivers distributed within the tracking environment is also provided, wherein the array of receivers includes a wide area receiver for receiving a plurality of substantially non-line-of-sight signals and a plurality of delimited area receivers. Each of the limited area receivers receives substantially line-of-sight signals.

A wide area detection packet is generated including the unique badge ID in response to each received higher power, wide area, non-line-of-sight signal. A local area detection packet is generated including the unique badge ID in response to each received lower power, local area, non-line-of-sight signal. The method further includes the step of generating a delimited area detection packet including the unique badge ID in response to each received line-of-sight signal. Finally, the method includes the step of determining the location of each badge and its associated subject based on the identity of the wide area and delimited area receivers for the badge as represented by its wide area, local area and delimited area detection packets.

Preferably, the line-of-sight and non-line-of-sight signals are electromagnetic transmissions such as infrared signals and radio frequency signals, respectively.

The IR and RF signals are encoded with badge identification data, push button switch, external switch status, and battery condition data. The system also includes ceiling or wall receivers in the form of IR and RF receivers. Each RF receiver converts the encoded high power RF signals into a first set of electrical signals and the encoded low power RF signals into a second set of electrical signals. Each IR receiver converts encoded IR signals into a third set of electrical signals. In turn, the first, second and third sets of electrical signals are transmitted to a microprocessor-based decoder of the system. The locating method and system are useful in locating subjects and providing the subjects a mechanism to generate notification of varying events in an environment such as a hospital or office building. The resulting location change and notification events can then be used to automate and increase the efficiency of ordinary day-to-day human processes.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for locating subjects within a tracking environment, the method comprising the steps of:
    for each subject, providing a badge capable of automatically transmitting a shorter interval, lower power, local area RF signal including a unique badge ID and a longer interval, higher power, wide area signal also including the unique badge ID separate from transmission of the local area RF signal;
    providing an array of receivers distributed within the tracking environment, wherein the array of receivers includes at least one receiver for receiving the shorter interval, lower power, local area signal and the longer interval, higher power, wide area signal;
    generating a wide area detection packet including the unique badge ID in response to each received wide area signal;
    generating a local area detection packet including the unique badge ID in response to each received local area signal; and
    determining the location of each badge and its associated subject based on the identity of the at least one receiver for the badge as represented by its local area or wide area detection packets.

2. The method of claim 1 wherein the signals are electromagnetic signals.

3. The method of claim 2 wherein the signals are radio frequency (RF) signals and the at least one receiver includes at least one RF receiver.

4. A system for locating subjects within a tracking environment, the system including:
    for each subject, a badge capable of automatically transmitting a shorter interval, lower power, local area RF signal including a unique badge ID and a longer interval, higher power, wide area signal also including the unique badge ID separate from transmission of the local area RF signal;
    a receiver assembly including an array of receivers distributed within the tracking environment, wherein the array of receivers includes at least one receiver for receiving a plurality of the local area and wide area signals, the receiver assembly generating a wide area detection packet including the unique badge ID in response to each received wide area signal and a local area detection packet including the unique badge ID in response to each received local area signal;
    a data communications controller coupled to the receiver assembly for collecting the wide area and local area detection packets; and
    a location processor coupled to the controller for receiving the collected detection packets and for determining the location of each badge and its associated subject based on the identity of the at least one receiver for the badge as represented by its wide area and local area detection packets.

5. The system as claimed in claim 4 wherein the signals are electromagnetic signals.

6. The system as claimed in claim 5 wherein the signals are radio frequency (RF) signals and the at least one receiver includes at least one RF receiver.

7. The system as claimed in claim 6 wherein each badge includes an RF transmitter for transmitting its RF signals and a single controller for controllably modulating both the local area and wide area signals with its unique badge ID.

8. The system as claimed in claim 7 wherein the single controller is a microprocessor-based controller.

9. The system as claimed in claim 6 wherein the receiver assembly includes a collector coupled to the at least one RF receiver for controllably demodulating the received RF signals to obtain the wide area and local area detection packets.

10. The system as claimed in claim 9 wherein the collector includes a single microprocessor for controllably demodulating the received RF signals.

11. A method for locating subjects within a tracking environment, the method comprising the steps of:
    for each subject, providing a badge capable of automatically transmitting substantially line-of-sight signals including a unique badge ID and substantially non-line-of-sight signals, each of the substantially non-line-of-sight signals also including the unique badge ID and being transmitted separately from each of the other substantially non-line-of-sight signals;
    providing an array of receivers distributed within the tracking environment, wherein the array of receivers includes: a first set of receivers for receiving both shorter interval, lower power, local area, substantially non-line-of-sight RF signals and longer interval, higher power, wide area, substantially non-line-of-sight signals; and a second set of receivers, each of the second set of receivers receiving substantially line-of-sight signals;
    generating a wide area detection packet including the unique badge ID in response to each received higher power, substantially non-line-of-sight signal;

generating a local area detection packet including the unique badge ID in response to each received lower power, substantially non-line-of-sight signal;

generating a delimited area detection packet including the unique badge ID in response to each received substantially line-of-sight signal; and determining the location of each badge and its associated subject based on the identity of the first and second sets of receivers for the badge as represented by its delimited area, local area or wide area detection packets.

12. The method of claim 11 wherein the substantially line-of-sight and non-line-of-sight signals are electromagnetic signals.

13. The method of claim 12 wherein the substantially non-line-of-sight signals are radio frequency (RF) signals and each of the first set of receivers is an RF receiver.

14. The method of claim 13 wherein the substantially line-of-sight signals are infrared (IR) signals and each of the second set of receivers is an IR receiver.

15. A system for locating subjects within a tracking environment, the system including:

for each subject, a badge capable of transmitting substantially line-of-sight signals including a unique badge ID and substantially non-line-of-sight signals each of the non-line-of-sight signals also including the unique badge ID and being transmitted separately from each of the other substantially non-line-of-sight signals and wherein at least one of the non-line-of-sight signals includes a automatically transmitted, lower power, substantially non-line-of-sight RF signal;

a receiver assembly including an array of receivers distributed within the tracking environment, wherein the array of receivers includes: a first set of receivers for receiving a plurality of substantially non-line-of-sight signals, the receiver assembly generating a wide area detection packet including the unique badge ID in response to each received higher power, substantially non-line-of-sight signal and a local area detection packet including the unique badge ID in response to each received lower power, substantially line-of-sight RF signal; the array of receivers also including a second set of receivers, each of the second set of receivers receiving substantially line-of-sight signals, the receiver assembly generating a delimited area detection packet including the unique badge ID in response to each received substantially line-of-sight signal;

a data communications controller coupled to the receiver assembly for collecting the wide area, local area and delimited area detection packets; and a location processor coupled to the controller for receiving the collected detection packets and for determining the location of each badge and its associated subject based on the identity of the first and second sets of receivers for the badge as represented by its wide area, local area or delimited area detection packets.

16. The system as claimed in claim 15 wherein the substantially line-of-sight and non-line-of-sight signals are electromagnetic signals.

17. The system as claimed in claim 16 wherein the substantially non-line-of-sight signals are radio frequency (RF) signals and each of the first set of receivers is an RF receiver.

18. The system as claimed in claim 17 wherein the substantially line-of-sight signals are infrared (IR) signals and each of the second set of receivers is an IR receiver.

19. The system as claimed in claim 18 wherein each badge includes an RF transmitter for transmitting its RF signals, an IR transmitter for transmitting its IR signals and a single controller for controllably modulating the RF and IR signals with its unique badge ID.

20. The system as claimed in claim 19 wherein the single controller is a microprocessor-based controller.

21. The system as claimed in claim 18 wherein the receiver assembly includes a collector coupled to the RF and IR receivers for controllably demodulating the received RF and IR signals to obtain the wide area, local area and delimited area detection packets.

22. The system as claimed in claim 21 wherein the collector includes a single microprocessor for controllably demodulating the received RF and IR signals.

23. A badge capable of transmitting substantially line-of-sight signals including a unique badge ID and substantially non-line-of-sight signals also including the unique badge ID, the badge comprising:

a first transmitter for transmitting a plurality of substantially non-line-of-sight signals including a longer interval, higher power, wide area, substantially non-line-of-sight signal and a shorter interval, lower power, local area, substantially non-line-of-sight RF signal wherein the RF signal is transmitted automatically and separately from the longer interval, higher power, wide area, substantially non-line-of-sight signal; and a second transmitter for transmitting a plurality of substantially line-of-sight signals.

24. The badge as claimed in claim 23 wherein the substantially line-of-sight and non-line-of-sight signals are electromagnetic signals.

25. The badge as claimed in claim 24 wherein the substantially non-line-of-sight signals are radio frequency (RF) signals.

26. The badge as claimed in claim 25 wherein the substantially line-of-sight signals are infrared (IR) signals.

27. The badge as claimed in claim 26 wherein the first transmitter includes an RF transmitter for transmitting the RF signals, and the second transmitter includes an IR transmitter for transmitting the IR signals and wherein the badge further comprises a single controller for controllably modulating the RF and IR signals with its unique badge ID.

28. The badge as claimed in claim 27 wherein the single controller is a microprocessor-based controller.

* * * * *